United States Patent [19]

Kordosky et al.

[11] Patent Number: 5,514,823
[45] Date of Patent: May 7, 1996

[54] BIS-(ALKYLSALICYLIDENE)ETHYLENE OR PHENYLENE DIAMINES AND TRANSITION METAL COMPLEXES THEREOF

[75] Inventors: Gary A. Kordosky; R. Brantley Sudderth, both of Tucson, Ariz.

[73] Assignee: Henkel Corporation, Plymouth Meeting, Pa.

[21] Appl. No.: 192,922

[22] Filed: Feb. 7, 1994

[51] Int. Cl.$^6$ ............ C07F 1/08; C07F 13/00; C07F 15/00
[52] U.S. Cl. ............ 556/32; 556/34; 564/274
[58] Field of Search ............ 564/274; 556/43, 556/113, 146, 32, 34

[56] References Cited

U.S. PATENT DOCUMENTS

| | | | |
|---|---|---|---|
| 2,301,861 | 11/1942 | Downing et al. | 564/274 |
| 2,533,205 | 12/1950 | Chenicek | 564/274 X |
| 3,756,943 | 9/1973 | Hopkins et al. | 208/143 |
| 3,895,041 | 7/1975 | Inman et al. | 564/274 X |
| 4,638,096 | 1/1987 | Virnig | 568/433 |
| 4,673,412 | 6/1987 | Stoldt et al. | 44/68 |
| 4,861,904 | 8/1989 | Sugie | 556/32 |
| 5,266,283 | 11/1993 | Friesen et al. | 556/32 X |
| 5,281,578 | 1/1994 | Bradley et al. | 556/32 X |

FOREIGN PATENT DOCUMENTS 1458695  12/1976  United Kingdom.

OTHER PUBLICATIONS

Nakamura et al, Chemical Abstracts, vol. 95 (1981) 141973t.
Rohrbach et al, Chemical Abstracts, vol. 91 (1979) 131167m.
Saeed et al, Chemical Abstracts, vol. 110 (1989) 47672a.
Chen et al, Chemical Abstracts, vol. 11 (1989) 49339s.
Oki et al, Chemical Abstracts, vol. 113 (1990) 144050r.
Xin, Chemical Abstracts, vol. 119 (1993) 285180u.

*Primary Examiner*—Richard L. Raymond
*Attorney, Agent, or Firm*—Ernest G. Szoke; Wayne C. Jaeschke; Patrick J. Span

[57] ABSTRACT

Preparation of N,N'-bis(alkylsalicylidene)ethylene or phenylene diamines, and transition metal complexes thereof, particularly copper, and their use as an additive to diesel fuel to reduce soot formation in diesel exhaust.

8 Claims, No Drawings

BIS-(ALKYLSALICYLIDENE)ETHYLENE OR PHENYLENE DIAMINES AND TRANSITION METAL COMPLEXES THEREOF

BACKGROUND OF THE INVENTION

1. Field of the Invention

This invention relates generally to novel N,N'-bis(alkyl salicylidene)ethylene or phenylene diamines and the transition metal complexes thereof, particularly Cu, Mn and Fe and the use of the complexes as an additive to diesel fuels.

2. Description of the Related Art

The use of various metal compounds, particularly transition metal compounds such as compounds of manganese, lead, copper, zinc, cobalt and nickel, to name a few, in fuels to reduce soot formation and improve combustion properties of the fuel is known. U.S. Pat. No. 4,673,412 teaches an oil-soluble, transition metal complex of a Mannich base and an oxime wherein the molar ratio of I:II is from about 1:10 to about 10:1 are useful in association with diesel fuels or fuel oils which give good storage stability and at the same time effectively reduce the ignition temperatures for soot particulates. The transition metal complexes of the N,N'-bis(alkylsalicylidene)ethylene or phenylene diamines according to the present invention are useful as additives in diesel fuel to reduce soot formation in diesel exhaust in the absence of mannich bases.

SUMMARY OF THE INVENTION

It has been surprisingly discovered that the transition metal complexes of N,N'-bis(alkylsalicylidene)ethylene or phenylene diamines are effective additives in fuels, especially diesel fuel, in reducing the soot content of the exhaust from the combustion of fuels containing the complexes. The N,N'-bis(alkylsalicylidene)ethylene or phenylene diamines according to the invention have the formula I

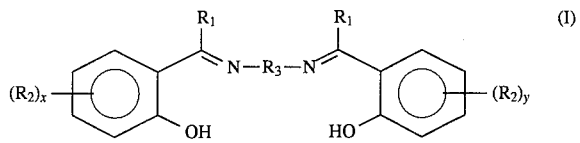

wherein $R_1$ is hydrogen or an alkyl group having from 1 to about 10 carbon atoms; $R_2$ is an alkyl group having from 1 to about 25 carbon atoms; $R_3$ is —$CH_2CH_2$— or

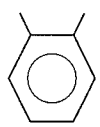

and x and y are integers from 1 to 3, preferably 1. $R_1$ is preferably hydrogen or methyl while $R_2$ is preferably an alkyl group having about 8 to about 15 carbon atoms. The total number of carbon atoms in the $R_1$ and $R_2$ groups should be sufficient to render the transition metal complexes thereof soluble in a diesel fuel such as kerosene. As a practical matter the total number of carbon atoms in the $R_1$ and $R_2$ groups will range from about 8 to about 50, preferably about 8 to about 30.

The transition metal complexes of the compounds of formula I have the formula II and III

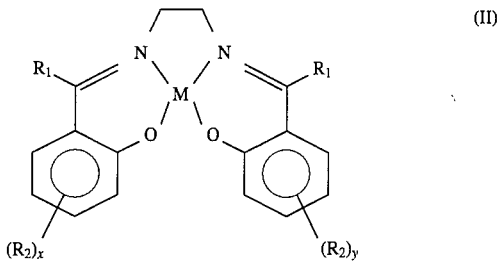

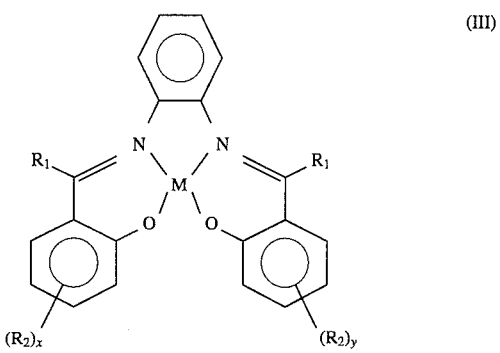

wherein $R_1$ and $R_2$, x and y are as defined above and M is a transition metal preferably Cu, Mn or Fe, with Cu being most preferred.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The N,N'-bis(alkylsalicylidene)ethylenediamines according to the invention are made by reacting alkyl substituted salicylaldehydes or alkyl substituted 2-hydroxyacetophenones with ethylenediamine in the presence of an acid catalyst such as para-toluenesulfonic acid and a solvent which serves as a reaction solvent and forms an azeotrope with water to effect the removal of the water of reaction such as toluene. The alkyl substituted salicylaldehydes can be made by the method taught in U.S. Pat. No. 4,638,096, the entire contents of which are incorporated herein by reference. The alkyl substituted acetophenones can be made by the method of British Patent GB 1,458,695, the entire contents of which are incorporated herein by reference. The transition metal complexes of the N,N'-bis(alkylsalicylidene)ethylenediamines according to the invention can be made by dissolving an N,N'-bis(alkylsalicylidene)ethylenediamine in an aliphatic or aromatic kerosene, such as, preferably, Escaid® 110, a trademark product of Exxon-U.S. An aqueous solution of a water soluble salt of the transition metal and ammonium hydroxide is then added to the kerosene solution and the combined liquid phases are stirred together for 2 hours at room temperature after which the 2 liquid phases are allowed to separate. The kerosene phase, which contains the metal complex, is then separated.

The transition metal complex is added to a diesel fuel or fuel oil in an amount to reduce soot formation, particularly in diesel exhaust, generally in an amount to provide up to about 200 ppm of the transition metal, preferably less than about 100 ppm, i.e. about 50 to about 100 ppm The following examples are meant to illustrate but not limit the invention.

EXAMPLE 1

Preparation of N,N'-bis(5-dodecylsalicylidene)ethylenediamine

Dodecylsalicylaldehyde (557 g, 93% pure 1.8 moles), ethylene diamine (54 g, 0.9 moles), para-toluenesulfonic acid hydrate (3.6 g, 0.02 moles), and toluene (1 liter) were combined in a 3-liter, 3-neck round bottom flask equipped with an overhead stirrer, a Dean-Stark trap, and a heating mantel. There was a slight exotherm (40 degrees C.) upon combining the starting materials. The reaction was then heated to reflux, accompanied by vigorous stirring. After 2.5 hours, 32 ml of water were collected in the Dean-Stark trap and the reaction allowed to cool. The reaction was poured into a large separatory funnel and washed twice with 2% sodium bicarbonate (300 mls) and twice with water (300 mls). The toluene was then removed under reduced pressure (rotoevaporation, 2 mbar/70° C., 3 hours) to yield 557 g of the final product. IR and NMR showed only a trace of starting aldehyde (<1%).

EXAMPLE 2

Preparation of N,N'-bis(5-nonylsalicylidene)ethylenediamine

The procedure of Example 1 was followed using nonylsalicylaldehyde (560 g, 93% pure, 2.1 moles), and ethylenediamine (63 g, 1.05 moles) to yield 555 g of final product.

EXAMPLE 3

Preparation of N,N'-bis(2-hydroxy-5-nonyl-α-methylbenzylidene)ethylenediamine The procedure of Example 1 was followed using 5-nonylhydroxyacetophenone (631 g, 83% pure, 2 moles) and ethylenediamine (60 g, 1 mole) to yield ca. 600 g of final product.

EXAMPLE 4

Preparation of the Copper Complex of N,N'-bis(5-dodecylsalicylidene)ethylenediamine N,N'-bis(5-dodecylsalicylidene)ethylenediamine (236 g, ca. 93% pure, 0.35 moles) was dissolved in 258 g of Escaid® 110 at 60° C. in a 2-liter round bottom flask. An aqueous solution of copper sulfate (500 g water; 85.6 g of $CuSO_4 \cdot 5H_2O$) and concentrated ammonium hydroxide (72 g of 30% in water) were added to the flask. The solution was stirred for 2 hours at room temperature using an overhead stirrer and the phases allowed to split overnight. In order to obtain a good phase split an additional 129 g of Escaid® 110 was added. The organic layer was separated and washed twice with 50 mls water. The organic solution was placed on a rotoevaporator at 20 mbar/70° C. for 2 hours to remove trace amounts of water. The loaded reagent in Escaid® 110 and the aqueous phase were analyzed for copper.
Loaded reagent in Escaid® 110:32,200 ug Cu/g
Aqueous phase:3,530 ug Cu/g

EXAMPLE 5

Preparation of the Copper Complex of N,N'-bis(5-nonylsalicylidene)ethylenediamine N,N'-bis(5-nonylsalicylidene)ethylenediamine (236 g, ca. 93% pure) was dissolved in 258 g of Escaid® 110 at 60° C. in a 2-liter round bottom flask. An aqueous solution of copper sulfate (500 g water; 85.6 g of $CuSO_4 \cdot 5H_2O$) and concentrated ammonium hydroxide (72 g of 30% in water) were added to the flask. The solution was stirred for 2 hours at room temperature using an overhead stirrer. The aqueous layer no longer possessed the indicative blue color, so an additional 100 ml of the $CuSO_4$ solution was added. The organic layer was separated and washed twice with 50 mls water. The organic solution was placed on a rotoevaporator at 20 mbar/70° C. for 2 hours to remove trace amounts of water. The loaded reagent in Escaid® 110 and the aqueous phase were analyzed for copper.
Loaded reagent in Escaid® 110:42,400 ug Cu/g
Aqueous phase:5,200 ug Cu/g

EXAMPLE 6

Preparation of the Copper Complex of N,N'-bis(2-hydroxy-5-nonyl-α-methylbenzylidene)ethylenediamine N,N'-bis(2-hydroxy-5-nonyl-α-methylbenzylidene)ethylenediamine (268 g, ca. 83% pure) was dissolved in 258 g of Escaid 110 at 60° C. in a 2-liter round bottom flask. An aqueous solution of copper sulfate (500 g water; 85.6 g of $CuSO_4 \cdot 5H_2O$) and concentrated ammonium hydroxide (72 g of 30% in water) were added to the flask. The solution was stirred for 2 hours at room temperature using an overhead stirrer. The phases were allowed to separate overnight. The organic layer was separated and washed twice with 50 mls water. The organic solution was placed on a rotoevaporator at 20 mbar/70° C. for 2 hours to remove trace amounts of water. The loaded reagent in Escaid® 110 and the aqueous phase were analyzed for copper.
Loaded reagent in Escaid® 110: 41,400 ug Cu/g
Aqueous phase:363 ug Cu/g

What is claimed is:

1. A transition metal complex of a compound selected from the group consisting of N,N'-bis (5-dodecylsalicylidene) ethylene diamine, N,N'-bis(5-nonylsalicylidene) ethylene diamine, N,N'-bis (2-hydroxy-5-Nonyl-α-methylbenzylidene) ethylene diamine, N,N'-bis(dodecylsalicylidene) phenylene diamine, N,N'-bis(5-nonylsalicylidene) phenylene diamine, N,N'-bis(2-hydroxy-5-nonyl-α-methylbenzylidene) phenylene diamine and said transition metal is selected from the group consisting of Cu, Mn and Fe.

2. A transition metal complex of a compound selected from the group consisting of N,N'-bis(2-hydroxy-5-alkyl-α-methylbenzylidene ethylene diamine and N,N'-bis(2-hydroxy-5-alkyl-α-methylbenzylidene phenylene diamine, in which the transition metal is selected from the group consisting of Cu, Mn and Fe and the alkyl group is selected from the group consisting of nonyl and dodecyl.

3. A transition metal complex of N,N'-bis(5-alkyl salicylidene) ethylene diamine in which the transition metal is selected from the group consisting of Cu, Mn and Fe and the alkyl group is selected from the group consisting of nonyl and dodecyl.

4. A transition metal complex of N,N'-bis(5-alkyl salicylidene) phenylene diamine in which the transition metal is selected from the group consisting of Cu, Mn and Fe and the alkyl group is selected from the group consisting of nonyl and dodecyl.

5. A transition metal complex of N,N'-bis(2-hydroxy-5-nonyl-α-methylbenzylidene ethylene diamine.

6. The copper complex of the compound defined in claim 1.

7. The Mn complex of the compound defined in claim 1.

8. The Fe complex of the compound defined in claim 1.

* * * * *